(12) United States Patent
Moon et al.

(10) Patent No.: US 9,605,347 B2
(45) Date of Patent: Mar. 28, 2017

(54) METHOD OF FORMING A FILM HAVING A SURFACE STRUCTURE OF RANDOM WRINKLES

(71) Applicant: ELECTRONICS AND TELECOMMUNICATIONS RESEARCH INSTITUTE, Daejeon (KR)

(72) Inventors: Jaehyun Moon, Daejeon (KR); Seung Koo Park, Daejeon (KR); Jeong Ik Lee, Gunpo-si (KR); Jin Wook Shin, Incheon (KR); Doo-Hee Cho, Daejeon (KR); Joo Hyun Hwang, Seoul (KR); Chul Woong Joo, Seoul (KR); Jun-Han Han, Daejeon (KR); Jin Woo Huh, Daejeon (KR); Joon Tae Ahn, Daejeon (KR); Nam Sung Cho, Daejeon (KR); Hye Yong Chu, Daejeon (KR); Byoung Gon Yu, Chungcheongbuk-do (KR)

(73) Assignee: ELECTRONICS AND TELECOMMUNICATIONS RESEARCH INSTITUTE, Daejeon (KR)

( * ) Notice: Subject to any disclaimer, the term of this patent is extended or adjusted under 35 U.S.C. 154(b) by 0 days.

(21) Appl. No.: 15/018,887

(22) Filed: Feb. 9, 2016

(65) Prior Publication Data

US 2016/0168712 A1 Jun. 16, 2016

Related U.S. Application Data

(63) Continuation of application No. 13/780,391, filed on Feb. 28, 2013, now abandoned.

(30) Foreign Application Priority Data

Jul. 25, 2012 (KR) .................. 10-2012-0081446
Oct. 19, 2012 (KR) .................. 10-2012-0116706

(51) Int. Cl.

| | | |
|---|---|---|
| C07C 43/205 | (2006.01) |
| C23C 16/56 | (2006.01) |
| C07C 43/225 | (2006.01) |
| F21V 3/04 | (2006.01) |
| C08F 136/20 | (2006.01) |
| C08F 12/20 | (2006.01) |
| C08F 12/34 | (2006.01) |
| C08G 65/00 | (2006.01) |
| C09D 125/18 | (2006.01) |

(52) U.S. Cl.
CPC ............ C23C 16/56 (2013.01); C07C 43/225 (2013.01); C08F 12/20 (2013.01); C08F 12/34 (2013.01); C08F 136/20 (2013.01); C08G 65/007 (2013.01); C09D 125/18 (2013.01); F21V 3/0409 (2013.01); *Y10T 428/24446* (2015.01)

(58) Field of Classification Search
USPC ........................................ 568/644, 645, 646
See application file for complete search history.

(56) References Cited

U.S. PATENT DOCUMENTS 7,202,324 B2 * 4/2007 Kim .................... C07C 43/225
                                                    524/544

FOREIGN PATENT DOCUMENTS

| KR | 10-2010-0067037 A | 6/2010 |
| KR | 10-1000120 B1 | 12/2010 |
| KR | 10-2011-0011468 A | 2/2011 |
| KR | 10-2011-0079911 A | 7/2011 |
| KR | 10-2012-0054887 A | 5/2012 |
| WO | WO 2010-051229 A2 | 5/2010 |

OTHER PUBLICATIONS

Jia; Optical materials; 2006, 28, 189-194.*
Seung Koo Park et al., "Highly fluorinated and photocrosslinkable liquid prepolymers for flexible optical waveguides", Journal of Materials Chemistry, 2011, 21, pp. 1755-1761, Feb. 14, 2011.

* cited by examiner

*Primary Examiner* — Pancham Bakshi
(74) *Attorney, Agent, or Firm* — Rabin & Berdo, P.C.

(57) ABSTRACT

Provided is a method of forming a film having a surface structure of a random wrinkles. A compound according to the present invention is coated and then, a film having a surface structure of random wrinkles may be simply formed through simple ultraviolet (UV) curing or thermosetting. When the film thus formed is used in an organic light emitting device, light generated from the organic light emitting device is scattered on surfaces of the random wrinkles to prevent light guide or total reflection, and thus, light is extracted to the outside. That is, a random structure disposed at the outside of the device performs a light extraction function and consequently, light efficiency of the organic light emitting device may be increased.

14 Claims, 6 Drawing Sheets

METHOD OF FORMING A FILM HAVING A SURFACE STRUCTURE OF RANDOM WRINKLES

CROSS-REFERENCE TO RELATED APPLICATIONS

This is a continuation of application Ser. No. 13/780,391, filed Feb. 28, 2013. Further, this U.S. non-provisional patent application claims priority under 35 U.S.C. §119 of Korean Patent Application Nos. 10-2012-0081446, filed on Jul. 25, 2012, and 10-2012-0116706, filed on Oct. 19, 2012. The entire contents of these prior applications are hereby incorporated by reference.

BACKGROUND

The present invention disclosed herein relates to a chemical compound being used for forming a random wrinkle structure, composition containing the compound, film having the structure, method of forming the film, and OLED comprising the film.

Films having a random wrinkle structure may be used in various fields. For example, such a structure may be used in an organic light emitting diode (OLED).

An organic light emitting diode is a self-luminous type device which emits light by electrically exciting an organic light emitting material. The organic light emitting diode includes a substrate, an anode, a cathode, and an organic light emitting layer formed between the anode and the cathode. Holes and electrons supplied from the anode and the cathode are combined in the organic light emitting layer to generate externally emitted light.

The organic light emitting diode is a device which is formed by physically stacking various elements such as a substrate, an organic layer, and a metal thin film. The light generated in the organic light emitting layer becomes visible light after passing through an interface between heterogeneous materials and films having different refractive indices. The light generated due to the interface and the different refractive indices may be guided or may be undergone a total reflection process. As a result, loss of about 80% of the light occurs in an OLED having a typical thin film stack structure and only about 20% of the light is emitted from the OLED device and obtained as visible light. An increase in applied voltage is inevitably required in order to secure above a predetermined level of brightness. The applied voltage results in negative consequence for the device broadly in terms of two aspects. First, energy consumption increases due to the increase in the applied voltage. Second, deterioration of the organic layer progresses in the case that the organic layer is continuously exposed in a high voltage and thus, lifetime of the device decreases. Therefore, there is a need for a technique that is able to effectively extract the generated light for the purpose of energy saving and longer lifetime. Technical approach performed to increase extraction efficiency of the generated light is commonly denoted as light extraction technology. The light extraction technology is generally classified as internal light extraction technology and external light extraction technology. A portion of the generated light becomes trapped due to the difference between refractive indices of the transparent anode and the substrate, and disappears by being guided between the anode and the substrate. In order to extract the light disappeared as above, there is a method of patterning irregular unevenness in a substrate for the possible light scattering in the substrate and the method is denoted as internal light extraction. The light entered into the substrate by the internal light extraction method may not escape from the inside of the substrate to an air layer due to the difference between refractive indices of the substrate and the air layer as described above, and thus, may disappear by being guided in the substrate. In order to extract the light disappeared as above to the outside of the air layer, a film or the like having unevenness etched therein is attached to an opposite side of the patterned unevenness and this is denoted as external light extraction. A film generally used for the external light extraction is a microlens array (MLA) film. With respect to the microlens array film, regularly patterned microlenses are formed on a film by using an imprinting method using an ultraviolet (UV)-curable material or an embossing method using a thermoplastic film. A block copolymer is used as a method of increasing light extraction by simply forming a random wrinkle structure on a film. The random wrinkle structure may be formed on a surface of the film by using a simple process employing the block copolymer, but depth and width of the random wrinkle structure may be relatively small, and thus, visible light may not be efficiently extracted.

SUMMARY

The present invention provides a compound able to form a random wrinkle structure.

The present invention also provides a composition including the compound.

The present invention also provides a film including a random wrinkle structure.

The present invention also provides a method of forming the film.

The present invention also provides an organic light emitting device including the film.

The object of the present invention is not limited to the aforesaid, but other objects not described herein will be clearly understood by those skilled in the art from descriptions below.

Embodiments of the present invention provide compounds having a structure of Chemical Formula 1, <Chemical Formula 1> where X is hydrogen or a halogen element, A is a cross-linking group, $Y_1$, $Y_2$, $Y_3$, $Y_4$, $Y_5$, $Y_6$, $Y_7$, $Y_8$, $Y_9$, $Y_{10}$, $Y_{11}$, $Y_{12}$, $Y_{13}$, $Y_{14}$, $Y_{15}$, $Y_{16}$, $Y_{17}$, and $Y_{18}$ are respectively any one group selected from the group consisting of -, —O—, —S—, —COO—, —CO—, —COS—, —SO$_2$—, —CONH—, and —NH—, $Z_{n,\,n+1}$ is a repeating number of an aliphatic or aromatic group disposed between $Y_n$ and $Y_{n+1}$ groups, n is 1, 2, 3, 4, 5, 7, 8, 9, 11, 12, 13, 15, 16, or 17, $Z_{n,\,n+1}$ is an integer between 0 and 100 when n=2, 3, 4, 7, 8, 11, 12, 15, and 16, $Z_{n,\,n+1}$ is 0 or 1 when n=1, 5, 9, 13, and 17, p is an integer between 1 and 10,000, and $Y_{n+1}$ is - when $Z_{n,\,n+1}$ is 0.

In some embodiments, the cross-linking group may have at least one structure selected from the group consisting of structures of the following chemical formulae.

In other embodiments, X may be hydrogen or fluorine and A may have a structure of

In still other embodiments, the compound may have any one structure selected from the group consisting of structures of the following chemical formulae, where q is an integer between 0 and 10,000.

In even other embodiments, the compound may be a liquid having a viscosity ranging from 1 cp to $1 \times 10^7$ cp at a temperature ranging from 0° C. to 50° C.

In other embodiments of the present invention, compositions including: the compound of Chemical Formula 1; and a curing initiator curing the compound, wherein an amount of the curing initiator may be included in a range of 0.1 wt % to 10 wt % based on a total weight, in which a weight of the compound and a weight of the curing initiator are added.

In some embodiments, the composition may further include a solvent diluting the compound, wherein an amount of the solvent may be included in a range of 1 wt % to 99 wt % based on the total weight of the composition.

In other embodiments, the solvent may be at least one selected from the group consisting of cyclopentanone, cyclohexanone, γ-butyrolactone, toluene, methanol, ethanol, ethyl ether, N,N-dimethyl acetamide, N-methyl pyrrodinone, tetrahydrofuran, ethyl acetate, and hexane.

In still other embodiments, the composition may further include a polymerization monomer, wherein an amount of the polymerization monomer may be included in a range of 0.1 wt % to 99.9 wt % based on the total weight of the composition.

In even other embodiments, the polymerization monomer may be at least one selected from the group consisting of 2,3,4,5,6-pentafluoro styrene, divinyl benzene, methyl methacrylate, methyl acrylate, trifluoroacetic acid allyl ester, trifluoroacetic acid vinyl ester, 2,2,2,-trifluoroethyl methacrylate, acrylic acid 1,1,1,3,3,3-hexafluoroisopropyl ester, methacrylic acid 1,1,1,3,3,3,-hexafluoroisopropyl ester, 1-pentafluorophenyl-pyrrole-2,5-dione, N-methyl maleimide, N-ethyl maleimide, N-propyl maleimide, N-butyl maleimide, N-tert-butyl maleimide, N-pentyl maleimide, and N-hexyl maleimide.

In other embodiments of the present invention, methods of forming a film having a random wrinkle structure including: coating a substrate with the composition; and curing the composition to form a film having a surface structure of random wrinkles.

In some embodiments, the curing initiator is a photocuring initiator, and the method may further include irradiating the composition with ultraviolet light. The irradiating with the ultraviolet light may be performed for 1 minute to 30 minutes in an inert gas atmosphere or vacuum. The method may further include thermally treating at a temperature ranging from 100° C. to 300° C., after the irradiating with the ultraviolet light.

In other embodiments, the curing initiator is a thermosetting initiator, and the method may further include thermally treating the composition at a temperature ranging from 50° C. to 100° C. The thermally treating may be performed for 5 minutes or more in an inert gas atmosphere or vacuum.

In still other embodiments, the method may further include thermally treating the composition at a temperature of 200° C. or more without an initiator. The thermally treating may be performed for 5 minutes or more in air, an inert gas atmosphere, or vacuum.

In even other embodiments of the present invention, films having a random wrinkle structure formed by three-dimensionally crosslinking compounds of Chemical Formula 1. A length of the wrinkles may be in a range of 200 nm to 1000 nm and a depth of the wrinkles may be in a range of 500 nm to 1000 nm. The film may have a refractive index ranging from 1.4 to 1.8.

In yet other embodiments of the present invention, organic light emitting devices including: a substrate including a first surface and a second surface facing each other; a first electrode, an organic light emitting layer, and a second electrode sequentially stacked on the first surface of the substrate; and a light scattering layer disposed on at least one of the second surface of the substrate and a surface of the second electrode, wherein the light scattering layer may be the same as the film.

BRIEF DESCRIPTION OF THE DRAWINGS

The accompanying drawings are included to provide a further understanding of the present invention, and are incorporated in and constitute a part of this specification. The drawings illustrate exemplary embodiments of the present invention and, together with the description, serve to explain principles of the present invention. In the drawings.

DETAILED DESCRIPTION OF THE EMBODIMENTS

Preferred embodiments of the present invention will be described below in more detail with reference to the accompanying drawings. Advantages and features of the present invention, and implementation methods thereof will be clarified through following embodiments described with reference to the accompanying drawings. The present invention may, however, be embodied in different forms and should not be construed as limited to the embodiments set forth herein. Rather, these embodiments are provided so that this disclosure will be thorough and complete, and will fully convey the scope of the present invention to those skilled in the art. Further, the present invention is only defined by scopes of claims. In the drawings, like reference numerals refer to like elements throughout.

In the following description, the technical terms are used only for explaining a specific exemplary embodiment while not limiting the present invention. The terms of a singular form may include plural forms unless referred to the contrary. The meaning of "comprises" and/or "comprising" specifies a property, a region, a fixed number, a step, a process, an element and/or a component but does not exclude other properties, regions, fixed numbers, steps, processes, elements and/or components. Since preferred embodiments are provided below, the order of the reference numerals given in the description is not limited thereto. In addition, it will be understood that when an element such as a layer, film, region, or substrate is referred to as being "on" another element, it can be directly on the other element or intervening elements may also be present.

A compound which may be used for forming a film having a random wrinkle structure according to the present invention has a structure of Chemical Formula 1.

$Y_{11}$, $Y_{12}$, $Y_{13}$, $Y_{14}$, $Y_{15}$, $Y_{16}$, $Y_{17}$, and $Y_{18}$ are respectively any one group selected from the group consisting of -, —O—, —S—, —COO—, —CO—, —COS—, —SO$_2$—, —CONH—, and —NH—, $Z_{n,\,n+1}$ is a repeating number of an aliphatic or aromatic group disposed between $Y_n$ and $Y_{n+1}$ groups, n is 1, 2, 3, 4, 5, 7, 8, 9, 11, 12, 13, 15, 16, or 17, $Z_{n,\,n+1}$ is an integer between 0 and 100 when n=2, 3, 4, 7, 8, 11, 12, 15, and 16, $Z_{n,\,n+1}$ is 0 or 1 when n=1, 5, 9, 13, and 17, p is an integer between 1 and 10,000, and $Y_{n+1}$ is - when $Z_{n,\,n+1}$ is 0.

Herein, a plurality of Xs are independently selected from hydrogen and a halogen element. For example, —CX$_2$—CX$_2$— may become —CH$_2$—CF$_2$— when the plurality of Xs are independently selected from hydrogen and fluorine. The phrase "a value of $Y_n$ or $Y_{n+1}$ is -" denotes "provision of a connection". For example, when $Y_n$ is - in R1-$Y_n$—R2, R1-$Y_n$—R2 becomes the same as R1-R2.

The cross-linking group may have at least one structure selected from the group consisting of structures of the following Chemical Formulae 2.

<Chemical Formulae 2>

<Chemical Formula 1> where X is hydrogen or a halogen element, A is a cross-linking group, $Y_1$, $Y_2$, $Y_3$, $Y_4$, $Y_5$, $Y_6$, $Y_7$, $Y_8$, $Y_9$, $Y_{10}$, As a specific example, X may be hydrogen or fluorine and A may have a structure of

For example, the compound may have any one structure selected from the group consisting of structures of the following Chemical Formulae 3.

<Chemical Formulae 3>

-continued where q is an integer between 0 and 10,000.

The compound may be a liquid having a viscosity ranging from 1 cp to $1 \times 10^7$ cp at a temperature ranging from 0° C. to 50° C.

The compound, a prepolymer, is a liquid phase and has two or more cross-linking groups at both ends. The compound has film-forming ability by polymerization after a curing process, is freely and three-dimensionally chemically bonded, and simultaneously undergoes a phase transition from a liquid phase to a solid phase. As a result, a volume of the compound shrinks and the compound may form a film having a surface structure of random wrinkles. The surface structure is spontaneously formed and may increase light extraction efficiency. Specifically, the film may have various functions, such as an external light extraction function, an internal light extraction function, an optical antiresonance function, a display pixel light extraction function, a low reflection function, a flexible light extraction function, and a water-repellent film coating function, and thus, may be used in various industrial fields.

The case in which the compound is used in a light scattering layer requiring an external light extraction function of an organic light emitting device will be described as a specific example.

Figure 1:
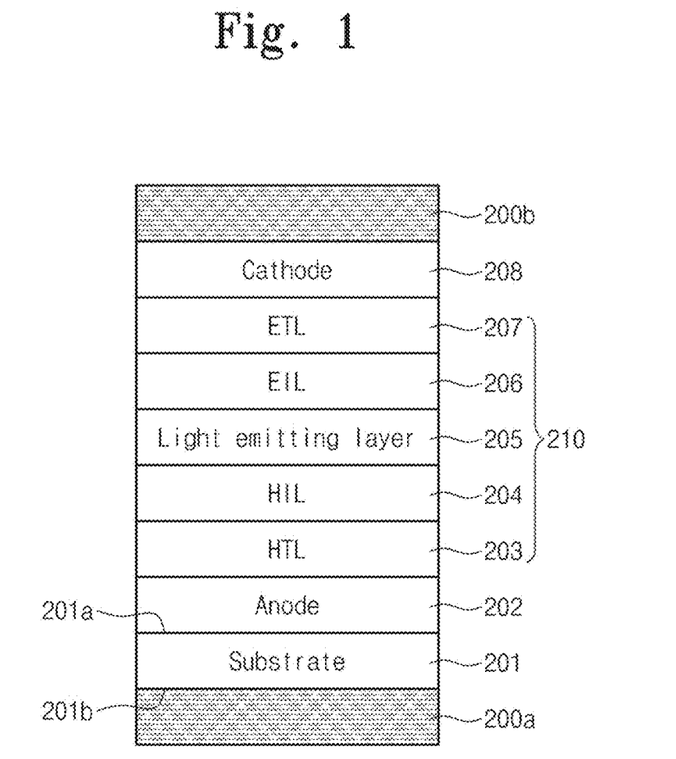
FIG. 1 is a cross-sectional view illustrating an organic light emitting device according to an embodiment of the present invention.

FIG. 1 is a cross-sectional view illustrating an organic light emitting device according to an embodiment of the present invention.

Referring to FIG. 1, a substrate 201 includes a first surface 201a and a second surface 201b facing each other. The substrate 201 may include at least one of glass, quartz, or plastic. The substrate 201 may be generally transparent, but may also be opaque in the case of a top-emission device. An anode 202, a hole transfer layer (HTL) 203, a hole injecting layer (HIL) 204, an organic light emitting layer 205, an electron injecting layer (EIL) 206, an electron transfer layer (ETL) 207, and a cathode (208) are sequentially stacked on the first surface 201a of the substrate 201. The cathode 208 may be selected from thin metal or conductive transparent oxide. As an example of the thin metal, a thin film including silver (Ag) may be selected and a thickness thereof may be in a range of about 5 nm to about 300 nm. The anode 202 may be a conductive material having transparency. For example, the anode 202 may be one of transparent conductive oxides (TCOs). For example, the anode 202 may be one of indium tin oxide (ITO) or indium zinc oxide (IZO). The hole transfer layer 203, the hole injecting layer 204, the organic light emitting layer 205, the electron injecting layer 206, and the electron transfer layer 207 may be formed by combination of organic compounds, metal complex compounds, and dopants. The hole transfer layer 203 through the electron transfer layer 207 may constitute an organic film 210.

Continuously, FIG. 1 is an example of a transparent organic light emitting device, in which light scattering layers 200a and 200b are respectively disposed on the second surface 201b of the substrate 201 and the cathode 208. The light scattering layers 200a and 200b have a surface structure of random wrinkles. A length of the wrinkles may be in a range of 200 nm to 1000 nm and a depth of the wrinkles may be in a range of 500 nm to 1000 nm. The light scattering layers 200a and 200b may have a refractive index ranging from 1.4 to 1.8. The foregoing conditions of the wrinkles and the refractive index of the light scattering layers 200a and 200b are necessary for efficient external light extraction. Also, in the case that surfaces of the light scattering layers 200a and 200b include regular wrinkles, since extraction dependency on a specific wavelength may occur similar to a photonic crystal structure, the surfaces thereof may have a random wrinkle structure.

Figure 2:
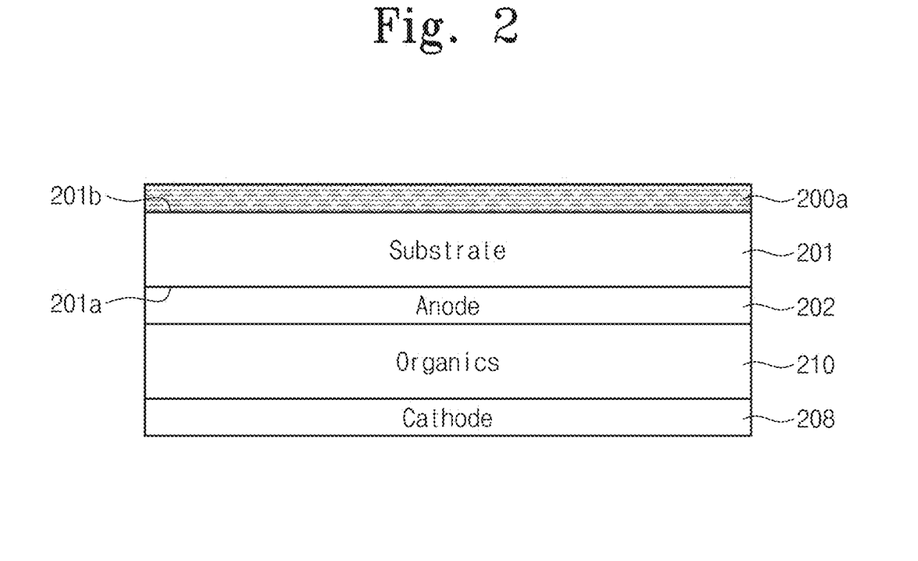
FIGS. 2 and 3 are cross-sectional views illustrating organic light emitting devices according to other embodiments of the present invention.
Figure 3:
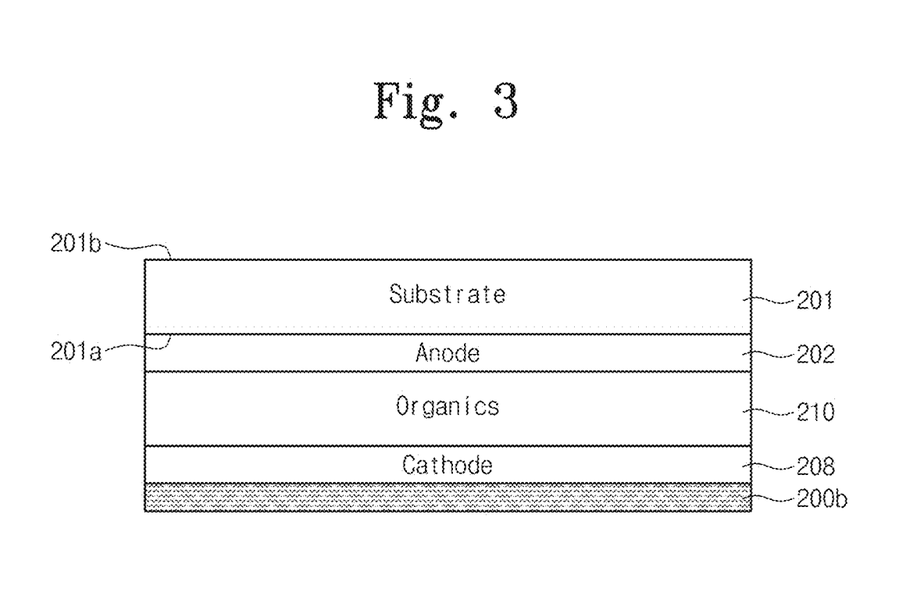

FIGS. 2 and 3 are cross-sectional views illustrating organic light emitting devices according to other embodiments of the present invention.

A light scattering layer 200a may be disposed only on a second surface 201b of a substrate 201 as in a bottom-emission organic light emitting device of FIG. 2. Also, a light scattering layer 200b may be disposed only on a cathode 208 as in a top-emission organic light emitting device of FIG. 3.

Figure 4A:
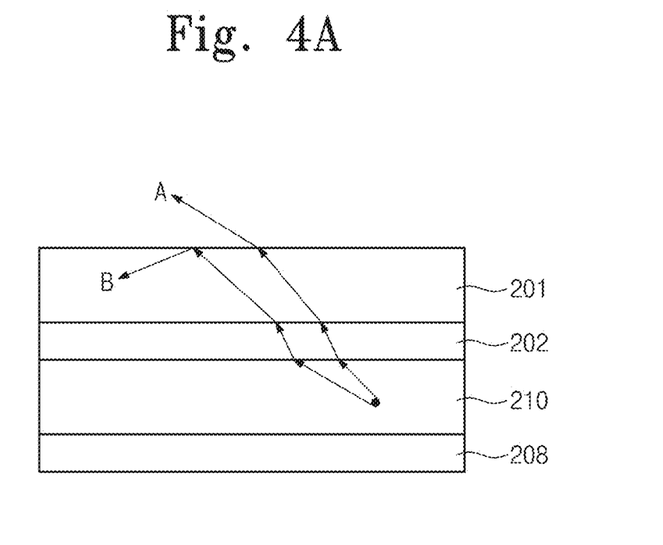
FIGS. 4A and 4B are cross-sectional views illustrating optical paths when a light scattering layer is absent or present, respectively.
Figure 4B:
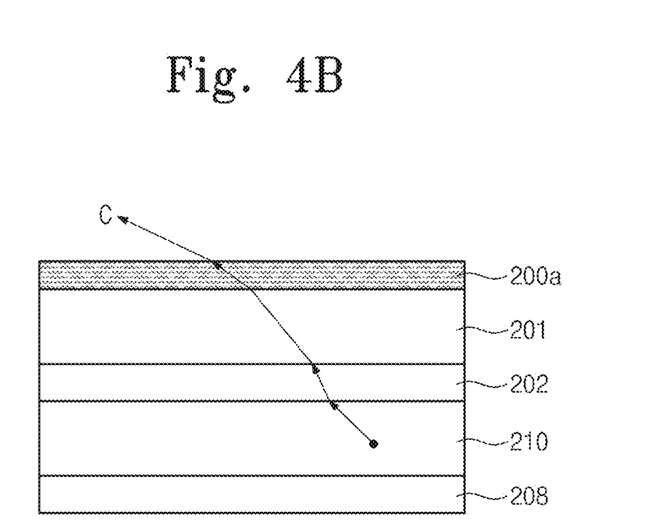

FIGS. 4A and 4B are cross-sectional views illustrating optical paths when a light scattering layer is absent or present, respectively. In the case that the light scattering layer 200a is not included as in FIG. 4A, generated light may not escape from the substrate to be visually recognized from the outside (light B) or may escape from the substrate 201 only in an optical path having an angle smaller than a total reflection angle (light A). As described with reference to FIG. 1, in the case that the light scattering layer 200a having a surface structure of random wrinkles is included, light C having an angle greater than the total reflection angle may also escape to the outside. The reason for this is that the random wrinkle structure may cause light scattering effects to induce external light extraction.

In FIGS. 4A and 4B, bottom-emission devices are exemplified as in FIG. 2, but the same approach may be applied to a top-emission device and a transparent light emitting device.

A process of forming the light scattering layers 200a and 200b will be described with reference to FIGS. 5A through 5D.

A composition including the compound of Chemical Formula 1 is prepared in order to form the light scattering layer. The composition may or may not include a curing initiator curing the compound of Chemical Formula 1. In the case that the curing initiator is included, an amount of the curing initiator may be included in a range of 0.1 wt % to 10 wt % based on a total weight, in which a weight of the compound and a weight of the curing initiator are added, and for example, may be included in a range of 0.5 wt % to 2.5 wt %. The curing initiator may be a photocuring initiator or a thermosetting initiator.

The composition may further include a polymerization monomer. The polymerization monomer may be a low molecular weight vinyl-based monomer and may further increase molecular weight after crosslinking of the prepolymers by acting as a chain extender.

An amount of the polymerization monomer may be included in a range of 0.1 wt % to 50 wt % based on the total weight of the composition. The polymerization monomer may be at least one selected from the group consisting of 2,3,4,5,6-pentafluoro styrene, divinyl benzene, methyl methacrylate, methyl acrylate, trifluoroacetic acid allyl ester, trifluoroacetic acid vinyl ester, 2,2,2,-trifluoroethyl methacrylate, acrylic acid 1,1,1,3,3,3-hexafluoroisopropyl ester, methacrylic acid 1,1,1,3,3,3,-hexafluoroisopropyl ester, 1-pentafluorophenyl-pyrrole-2,5-dione, N-methyl maleimide, N-ethyl maleimide, N-propyl maleimide, N-butyl maleimide, N-tert-butyl maleimide, N-pentyl maleimide, and N-hexyl maleimide.

The composition may further include a solvent diluting the compound and an amount of the solvent may be included in a range of 1 wt % to 99 wt % based on the total weight of the composition.

The solvent may be at least one selected from the group consisting of cyclopentanone, cyclohexanone, γ-butyrolactone, toluene, methanol, ethanol, ethyl ether, N,N-dimethyl acetamide, N-methyl pyrrodinone, tetrahydrofuran, ethyl acetate, and hexane.

Viscosity and refractive index of the composition may be easily changed according to a mixing ratio of the compound, the polymerization monomer, and/or the solvent.

Figure 5A:
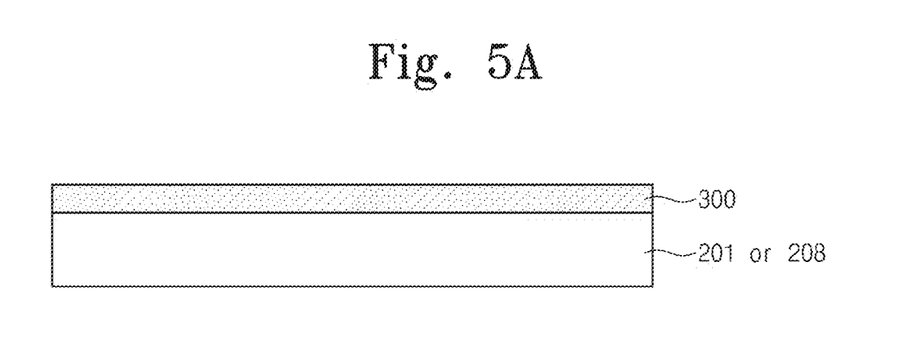
FIGS. 5A through 5D are cross-sectional views illustrating methods of forming a light scattering layer according to the present invention.

The composition is prepared and a support layer 201 or 208 is then coated with the composition 300 in order to form a light scattering layer with reference to FIG. 5A. The support layer 201 or 208 may be the substrate 201 or the cathode 208. Impurities in the composition may be removed by using a filter before coating with the composition. A spin coating method or a doctor knife may be used to coat the support layer 201 or 208 with the composition. The support layer 201 or 208 is coated with the composition and the composition is then cured.

A curing process of the composition may be changed according to a type of the curing initiator.

Figure 5B:
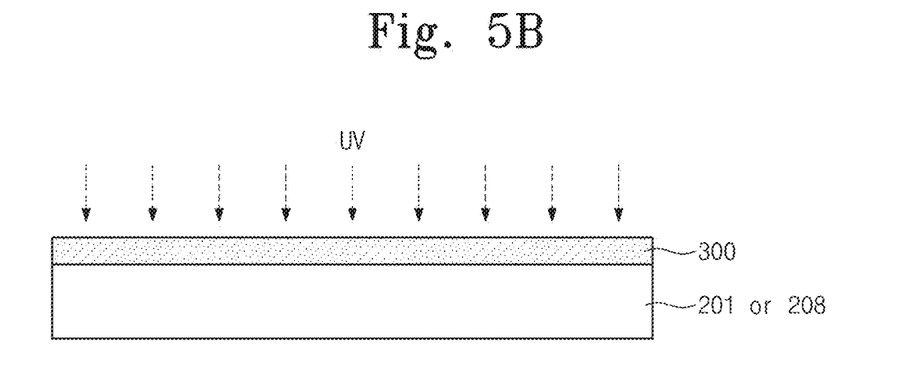

For example, in the case that the curing initiator is a photocuring initiator, the composition 300 is irradiated with ultraviolet (UV) light in order to cure the composition 300 with reference to FIG. 5B. The irradiation of the UV light may be performed for 1 minute to 30 minutes in an inert gas atmosphere, such as nitrogen, or in a vacuum state. A heat treatment may be further preformed on the cured composition at a temperature ranging from 100° C. to 300° C. after the irradiation of the UV light. The heat treatment at this time may also be performed in an inert gas atmosphere, such as nitrogen, or in a vacuum state.

Figure 5C:
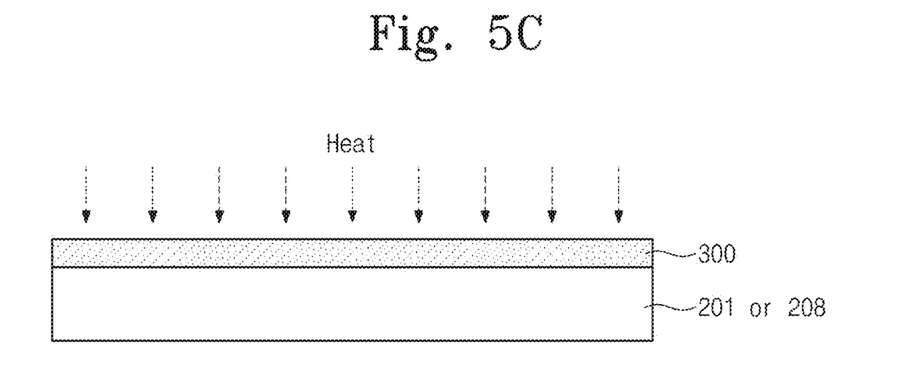

As another example, in the case that the curing initiator is a thermosetting initiator, a heat treatment may preformed on the cured composition 300 at a temperature ranging from 50° C. to 100° C. in order to cure the composition 300 with reference to FIG. 5C. The heat treatment may be performed for 5 minutes or more in an inert gas atmosphere or vacuum. For example, the heat treatment may be performed at a temperature ranging from about 100° C. to about 300° C. for 0.5 hours to 2 hours.

As another example, the curing process of the composition may be performed without a curing initiator. For example, a heat treatment may preformed on the cured composition 300 at a temperature of 200° C. or more for 5 minutes or more in air, an inert gas atmosphere, or vacuum in order to cure the composition 300.

Figure 5D:
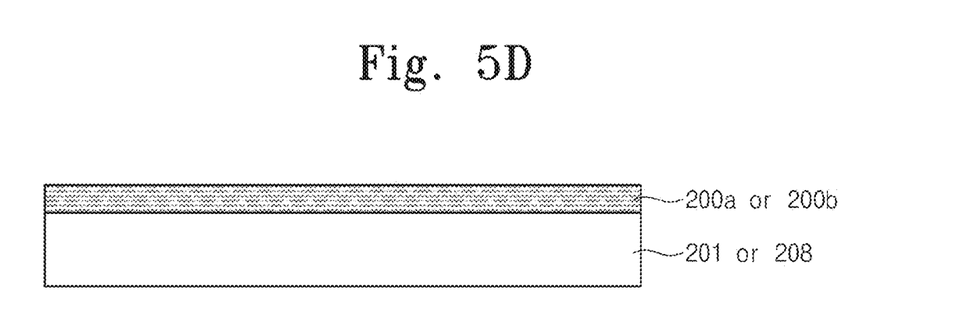

Referring to FIG. 5d, the compounds of Chemical Formula 1 in the composition 300 are three-dimensionally crosslinked through the foregoing curing process to form the light scattering layer 200a or 200b having a surface structure of random wrinkles and thus, visible light may be scattered. A length of the wrinkles may be in a range of 200 nm to 1000 nm and a depth of the wrinkles may be in a range of 500 nm to 1000 nm. The light scattering layer may have a refractive index ranging from 1.4 to 1.8. The foregoing conditions of the wrinkles and the refractive index of the light scattering layer are necessary for efficient external light extraction. Also, in the case that a surface of the light scattering layer includes regular wrinkles, since extraction dependency on a specific wavelength may occur similar to a photonic crystal structure, the surface thereof may have a random wrinkle structure.

Hereinafter, experimental examples of the present invention will be described.

Experimental Example 1

Synthesis of Prepolymer (3)

[Reaction Formula 1]

15.0 g of fluorinated tetraethylene glycol (1) and 14.2 g of 2,3,4,5,6-pentafluorostyrene (2) were dissolved in 50 ml of anhydrous N,N-dimethyl acetamide (DMAc) under a nitrogen flow in a 250 ml two-neck flask and 15.0 g of potassium carbonate was added as a reaction catalyst. A reaction was performed at a temperature ranging from 80° C. to 90° C. for about 24 hours in a nitrogen atmosphere. A temperature of a reaction solution after the termination of the reaction was decreased to room temperature, and potassium carbonate was then removed and the reaction solution was immersed in distilled water. A reactant was extracted with ethyl acetate (EA) and ethyl acetate was evaporated, and the brown reactant thus obtained was then purified by using a column having ethyl acetate/hexane (1/5, v/v) as a developer to obtain a transparent and colorless liquid-phase reactant (prepolymer (3)). Prepolymer (3) was then vacuum dried at 35° C. for 48 hours. At this time, a weight of prepolymer (3) thus obtained was 21.5 g and yield was about 77%. Prepolymer (3) was measured by infrared (IR), $^1$H nuclear magnetic resonance (NMR), and $^{19}$F NMR, and the results of the measurements are presented below.

IR (KBr, cm$^{-1}$): 3374 (m, O—H str., hydroxyl); 3038 (w, =C—H str., vinyl); 2965 (w, C—H str., methylene); 1291, 1119 (s, C—O str., ether).

$^1$H NMR (Chloroform-d$_1$, ppm): 6.69-6.59 (m, 1H, vinyl); 6.10-5.68 (m, 2H, vinyl); 4.53 (t, 2H, methylene); 3.96 (m, 2H, methylene); 2.74 (s, 1H, hydroxyl).

$^{19}$F NMR (Chloroform-d$_1$, ppm): −78.70 (m, 2F); −80.95 (m, 2F); −89.08 (m, 4F); −144.45 (m, 2F); −158.17 (m, 2F).

Experimental Example 2

Synthesis of Prepolymer (5)

[Reaction Formula 2]

(5)

8.0 g of tetraethylene glycol (4) and 16.0 g of 2,3,4,5,6-pentafluorostyrene (2) were dissolved in 40 ml of anhydrous N,N-dimethyl acetamide under a nitrogen flow in a 250 ml two-neck flask and 17.0 g of potassium carbonate was added as a reaction catalyst. A reaction was performed at room temperature for about 48 hours. Potassium carbonate was removed after the termination of the reaction and a reaction solution was immersed in distilled water. A reactant was extracted with ethyl acetate and ethyl acetate was evaporated, and the brown reactant thus obtained was then purified by using a column having ethyl acetate/hexane (1/1, v/v) as a developer to obtain a transparent and colorless liquid-phase reactant (prepolymer (5)). Prepolymer (5) was then vacuum dried at 35° C. for 48 hours. At this time, a weight of prepolymer (5) thus obtained was 7.4 g and yield was about 33%. Prepolymer (5) was measured by IR, $^1$H NMR, and $^{19}$F NMR, and the results of the measurements are presented below.

IR (KBr, cm$^{-1}$): 3374 (m, O—H str., hydroxyl); 3038 (w, =C—H str., vinyl); 2965 (w, C—H str., methylene); 1291, 1119 (s, C—O str., ether).

$^1$H NMR (Chloroform-d$_1$, ppm): 6.69-6.59 (m, 1H, vinyl); 6.10-5.68 (m, 2H, vinyl); 4.53 (t, 2H, methylene); 3.96 (m, 2H, methylene); 2.74 (s, 1H, hydroxyl).

$^{19}$F NMR (Chloroform-d$_1$, ppm): −78.70 (m, 2F); −80.95 (m, 2F); −89.08 (m, 4F); −144.45 (m, 2F); −158.17 (m, 2F).

Experimental Example 3

Synthesis of Prepolymer (7)

[Reaction Formula 3]

10.0 g of fluorinated tetraethylene glycol (6) and 13.2 g of 2,3,4,5,6-pentafluorostyrene (2) were dissolved in 40 ml of anhydrous DMAc under a nitrogen flow in a 250 ml two-neck flask and 14.0 g of potassium carbonate was added as a reaction catalyst. A reaction was performed at a temperature ranging from 80° C. to 90° C. for about 24 hours in a nitrogen atmosphere. A temperature of a reaction solution after the termination of the reaction was decreased to room temperature, and potassium carbonate was then removed and the reaction solution was immersed in distilled water. A reactant was extracted with ethyl acetate and ethyl acetate was evaporated, and the brown reactant thus obtained was then purified by using a column having ethyl acetate/hexane (1/5, v/v) as a developer to obtain a transparent and colorless liquid-phase reactant (prepolymer (7)). Prepolymer (7) was then vacuum dried at 35° C. for 48 hours. At this time, a weight of prepolymer (7) thus obtained was 16.0 g and yield was about 73%. Prepolymer (7) was measured by IR, $^1$H NMR, and $^{19}$F NMR, and the results of the measurements are presented below.

IR (KBr, cm$^{-1}$): 3374 (m, O—H str., hydroxyl); 3038 (w, =C—H str., vinyl); 2965 (w, C—H str., methylene); 1291, 1119 (s, C—O str., ether).

$^1$H NMR (Chloroform-d$_1$, ppm): 6.69-6.59 (m, 1H, vinyl); 6.10-5.68 (m, 2H, vinyl); 4.53 (t, 2H, methylene); 3.96 (m, 2H, methylene); 2.74 (s, 1H, hydroxyl).

$^{19}$F NMR (Chloroform-d$_1$, ppm): −78.70 (m, 2F); −80.95 (m, 2F); −89.08 (m, 4F); −144.45 (m, 2F); −158.17 (m, 2F).

Experimental Example 4

Figure 6A:
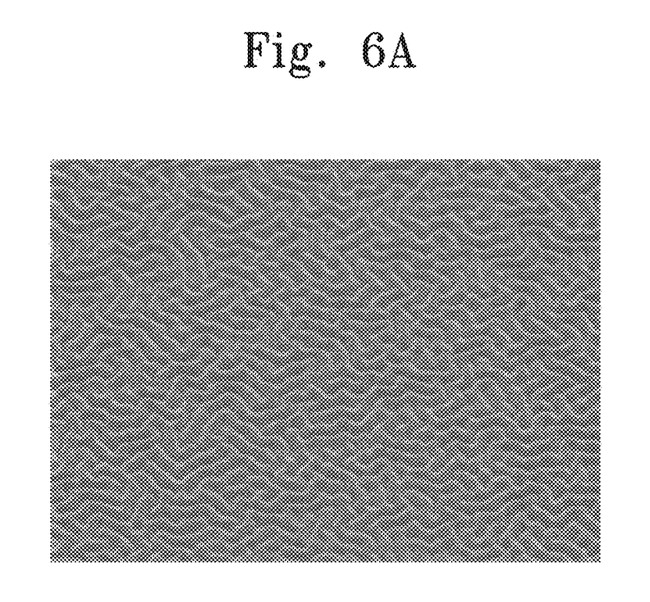
FIGS. 6A and 6B are a scanning electron microscope (SEM) micrograph and an atomic force microscope (AFM) image of a light scattering layer obtained from a prepolymer according to an experimental example of the present invention, respectively.
Figure 6B:
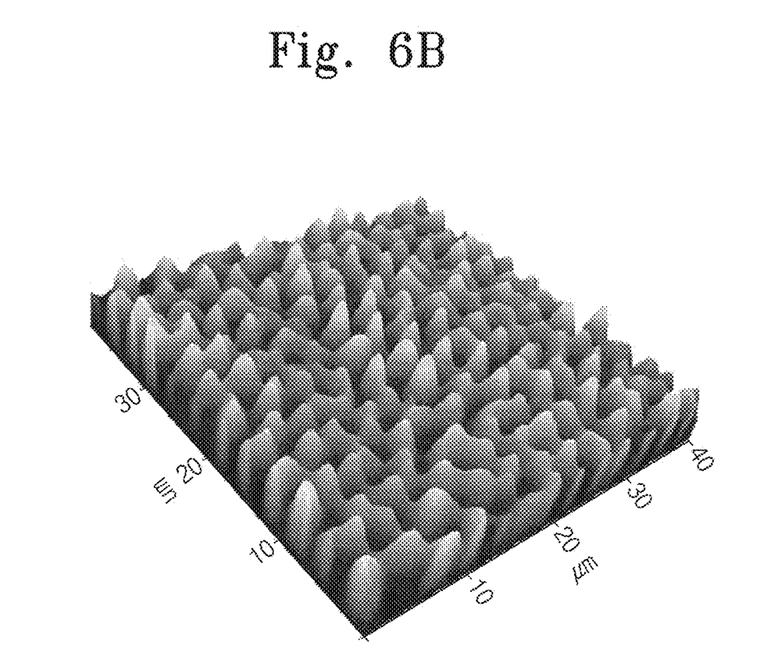

Preparation of Light Scattering Layer 0.9 g of liquid-phase prepolymer (3) prepared in Experimental Example 1 was diluted in 2.1 g of ethyl acetate to prepare a solution. A mixed photoinitiator of Igracure 184 and CGI 124 (8:2, wt %) was completely dissolved in the solution. At this time, an amount of the mixed photoinitiator was controlled to be 1.5 wt % based on a total weight in which a weight of prepolymer (3) and a weight of the mixed photoinitiator were added. A composition was formed by dissolving the mixed photoinitiator in the solution. The composition was passed through a 0.2 μm porous filter layer to completely remove undissolved fine particles, and a silicon wafer was then spin coated with a remaining filtrate at a speed of 3000 rpm for 30 seconds and exposed with ultraviolet light for 10 minutes to obtain a thin film having a random wrinkle structure. A scanning electron microscope (SEM) image and an atomic force microscope (AFM) image of the thin film obtained from prepolymer (3) were presented in FIGS. 6A and 6B, respectively. A surface state having random wrinkles may be confirmed in FIGS. 6A and 6B. At this time, surface roughness (Ra) was about 35 nm.

A prepolymer, a compound of Chemical Formula 1 according to the present invention, is coated and then, a film having a surface structure of random wrinkles may be simply formed by simple UV curing or thermosetting. When the film thus formed is used in an organic light emitting device, light generated from the organic light emitting device is scattered on surfaces of the random wrinkles to prevent light guide or total reflection, and thus, the light is extracted to the outside. That is, a random structure disposed at the outside of the device performs a light extraction function and consequently, light efficiency of the organic light emitting device may be increased.

While preferred embodiments of the present invention has been particularly shown and described with reference to the accompanying drawings, it will be understood by those of ordinary skill in the art that various changes in form and details may be made therein without departing from the spirit and scope of the present invention as defined by the following claims. Therefore, the preferred embodiments should be considered in descriptive sense only and not for purposes of limitation.

What is claimed is:

1. A method of forming a film having a surface structure of random wrinkles, the method comprising:
coating a substrate with a composition comprised of a compound having a structure selected from the group consisting of

-continued and where q is an integer of 0 to 10,000; and
curing the composition to form a film having said surface structure of random wrinkles.

2. The method of claim 1, wherein the compound is a liquid having a viscosity ranging from 1 cp to $1 \times 10^7$ cp at a temperature ranging from 0° C. to 50° C.

3. The method of claim 1, wherein the composition further comprises a solvent for diluting the compound that is present in an amount ranging from 1 wt % to 99 wt % based on total weight of the composition.

4. The method of claim 3, wherein the solvent is at least one solvent selected from the group consisting of cyclopentanone, cyclohexanone, γ-butyrolactone, toluene, methanol, ethanol, ethyl ether, N,N-dimethyl acetamide, N-methyl pyrrodinone, tetrahydrofuran, ethyl acetate, and hexane.

5. The method of claim 1, wherein the composition further comprises a polymerization monomer that is present in an amount ranging from 0.1 wt % to 99.9 wt % based on the total weight of the composition.

6. The method of claim 5, wherein the polymerization monomer is at least one monomer selected from the group consisting of 2,3,4,5,6-pentafluoro styrene, divinyl benzene, methyl methacrylate, methyl acrylate, trifluoroacetic acid allyl ester, trifluoroacetic acid vinyl ester, 2,2,2,-trifluoroethyl methacrylate, acrylic acid 1,1,1,3,3,3-hexafluoroisopropyl ester, methacrylic acid 1,1,1,3,3,3,-hexafluoroisopropyl ester, 1-pentafluorophenyl-pyrrole-2,5-dione, N-methyl maleimide, N-ethyl maleimide, N-propyl maleimide, N-butyl maleimide, N-tert-butyl maleimide, N-pentyl maleimide, and N-hexyl maleimide.

7. The method of claim 1, wherein the composition further comprises a photocuring initiator present in an amount ranging from 0.1 wt % to 10 wt % based on total weight of the compound and the photocuring initiator; and
curing the composition is accomplished by irradiating the composition with ultraviolet light.

8. The method of claim 7, wherein irradiating with ultraviolet light is performed for 1 minute to 30 minutes in an inert gas atmosphere or vacuum.

9. The method of claim 7, further comprising thermally treating at a temperature ranging from 100° C. to 300° C., after the irradiating with ultraviolet light.

10. The method of claim 1, wherein the composition further comprises a thermosetting initiator that is present in an amount ranging from 0.1 wt % to 10 wt % based on total weight of the compound and the thermosetting initiator; and
wherein the method further comprises thermosetting the composition at a temperature ranging from 50° C. to 100° C.

11. The method of claim 10, wherein thermosetting is performed for 5 minutes or more in an inert gas atmosphere or under a vacuum.

12. The method of claim 10, further comprising thermally treating at a temperature ranging from 100° C. to 300° C., after thermosetting.

13. The method of forming a film having a surface structure of random wrinkles, the method comprising:
coating a substrate with a composition comprising a compound having a structure of Chemical Formula 1 as follows;
curing the composition to form a film having said surface structure of random wrinkles, and
thermally treating the composition at a temperature of 200° C. or more, Chemical Formula 1 where X is hydrogen or a halogen element;

A is a cross-linking group;

$Y_1, Y_2, Y_3, Y_4, Y_5, Y_6, Y_7, Y_8, Y_9 Y_{10}, Y_{11}, Y_{12}, Y_{13}, Y_{14}, Y_{15}, Y_{16}, Y_{17}$, and $Y_{18}$ are respectively any one group selected from the group consisting of -, —O—, —S—, —COO—, —CO—, —COS—, —SO$_2$—, —CONH—, and —NH—;

$Z_{2,3}, Z_{3,4}, Z_{4,5} Z_{7,8} Z_{8,9} Z_{11,12} Z_{12,13} Z_{15,16}$, and $Z_{16,17}$ are respectively a repeating number and an integer of 0 to 100;

$Z_{1,2}, Z_{5,6}, Z_{9,10}, Z_{17,18}$ are respectively a repeating number and an integer of 0 or 1;

p is an integer of 1 to 10,000;

$Y_{n+}$ is - when $Z_{n,n+1}$ is 0, and n is 1,2,3,4,5,6,7,8,9,11,12,13,15,16, or 17, wherein the composition does not comprise an initiator; and the method further comprises thermally treating the composition at a temperature of 200° C. or more.

14. The method of claim 13, wherein thermally treating is performed for 5 minutes or more in air, an inert gas atmosphere, or vacuum.

* * * * *